US006267945B1

(12) United States Patent
Zamponi

(10) Patent No.: US 6,267,945 B1
(45) Date of Patent: Jul. 31, 2001

(54) FARNESOL-RELATED CALCIUM CHANNEL BLOCKERS

(75) Inventor: Gerald W. Zamponi, Calgary (CA)

(73) Assignee: NeuroMed Technologies, Inc., Vancouver (CA)

( * ) Notice: Subject to any disclaimer, the term of this patent is extended or adjusted under 35 U.S.C. 154(b) by 0 days.

(21) Appl. No.: 09/215,783

(22) Filed: Dec. 18, 1998

(51) Int. Cl.$^7$ ..................................................... A61K 49/00
(52) U.S. Cl. ............................ 424/9.1; 514/743; 514/760; 424/9.2
(58) Field of Search ..................................... 514/743, 746, 514/757, 758, 759, 760, 744, 745, 761, 816, 817, 818, 821, 824, 929; 424/9.1, 9.2

(56) References Cited

U.S. PATENT DOCUMENTS 5,386,025   1/1995   Jay et al. ............................. 536/23.5

FOREIGN PATENT DOCUMENTS

| 0 476682A | 3/1992 | (EP) . |
| 0 609440A | 8/1994 | (EP) . |
| 1403851A | 8/1975 | (GB) . |
| 62-093225A | 4/1987 | (JP) . |
| 7-126202A | 5/1995 | (JP) . |
| 8-176083A | 7/1996 | (JP) . |
| WO 98 02182A | 1/1998 | (WO) . |
| WO 98 54123A | 12/1998 | (WO) . |

OTHER PUBLICATIONS

Roullet et al, J. Clin. Invest., vol. 97, No. 10, pp. 2384–2390, "Farnesyl Analogues Inhibit Vasoconstriction in Animal and Human Arteries", May 15, 1996.*

Roullet et al, Hypertension, vol. 28, No. 3, p. 519, Abstract II 63, "Farnesyl Analogs Inhibit $Ca^{2+}$ Signaling in Smooth Muscle Cells and Arteries", Sep. 1996.*

Roullet et al, Hypertension, vol. 26, No. 3, p. 568, Abstract II P100, "Fainesol, a Non–Sterol derivative of Mevalonic Acid (MVA) is a potent Vasodilator", Sep. 1995.*

Roullet et al, FASEB, Journal, vol. 10, No. 3, A696, Abstract II 4021, "Farnesol inhibits arginine–vasopressin (AVP) response in rat resistance arteries and vascular smooth muscle cells (VSMC)," Apr. 14–17, 1996.*

Roullet et al, J. Biological Chemistry, vol. 272, No. 51, pp. 32240–32246, "Farnesol Inhibits L–type $Ca^{2+}$ channels in vascular smooth muscle cells," Dec. 19, 1997.*

Roulett J.B. et al. (1996). "Farnesyl Analogues Inhibit Vasoconstriction in Animal and Human Arteries," *Journal of Clinical Investigation* 97 (10):2384–2390.

Roulett J.B. et al. (1999). "Modulation of Neuronal Voltage–gated Calcium Channels by Farnesol," *J. Biol Chem* 274 (36):25439–25446.

Bech–Hansen et al., "Loss–of–Function Mutations in a Calcium–Channel $\alpha_1$–Subunit Gene in Xp11.23 Cause Incomplete X–linked Congenital Stationary Night Blindness," Nature Genetics (1998) 19:264–267.

De Waard et al., "Structural and Functional Diversity of Voltage–Activated Calcium Channels," Ion Channels (1997) vol. 4:41–87 (Plenum Press, NY).

Dunlap et al., "Exocytotic $Ca^{2+}$ Channels in Mammalian Central Neurons," Trends Neurosci. (1995) 18:89–98.

McClesky et al., "Functional Properties Of Voltage–Dependent Calcium Channels," Current Topics in Membranes (1991) 39:295–326.

Perez–Reyes et al., "Molecular Characterization of a Neuronal Low–Voltage–Activated T–type Calcium Channel," Nature (1998) 391:896–900

Roullet et al, "Farnesol Inhibits L–type $Ca^{2+}$ Channels in Vascular Smooth Muscle Cells," J. Biol. Chem. (1997) 272(51):32240–32246.

Sather et al., "Distinctive Biophysical And Pharmacological Properties of Class A (BI) Calcium Channel $\alpha_1$ Subunits," Neuron (1993) 11:291–303.

Stea et al., "Localization and Functional Properties of a Rat Brain $\alpha_{1A}$ Calcium Channel Reflect Similarities to Neuronal Q– and P–type Channels," Proc. Natl. Acad. Sci. USA (1994) 91:10576–10580.

* cited by examiner

Primary Examiner—Dameron L. Jones
(74) Attorney, Agent, or Firm—Morrison & Foerster LLP

(57) ABSTRACT

Compounds comprising
  a straight backbone carbon chain of 8–16C, optionally substituted with 1–5 alkyl groups (1–6C);
  said chain optionally functionalized at one terminus with halo, —OR, —SR, —NR$_2$, —OOCR, —NROCR wherein R is alkyl (1–6C), or phosphate or pyrophosphate, or functionalized wherein a terminal carbon is optionally in the form of —COOR, —CONR$_2$ or —COR wherein R is alkyl (1–6C); and
  wherein said chain may optionally contain 1–π-bonds or the epoxides thereof
are useful as calcium channel inhibitors. Libraries of these compounds can also be used to identify antagonists for other targets.

17 Claims, 5 Drawing Sheets

FARNESOL-RELATED CALCIUM CHANNEL BLOCKERS

TECHNICAL FIELD

The invention relates to compounds useful in treating conditions associated with calcium channel function. More specifically, the invention concerns compounds related to farnesol that are useful in treatment of conditions such as stroke and pain.

BACKGROUND ART

Native calcium channels have been classified by their electrophysiological and pharmacological properties as T, L, N, P and Q types (for reviews see McCleskey, E. W. et al. *Curr Topics Membr* (1991) 39:295–326, and Dunlap, K. et al. *Trends Neurosci* (1995) 18:89–98). T-type (or low voltage-activated) channels describe a broad class of molecules that transiently activate at negative potentials and are highly sensitive to changes in resting potential. The L, N, P and Q-type channels activate at more positive potentials and display diverse kinetics and voltage-dependent properties. There is some overlap in biophysical properties of the high voltage-activated channels, consequently pharmacological profiles are useful to further distinguish them. L-type channels are sensitive to dihydropyridine agonists and antagonists, N-type channels are blocked by the *Conus geographus* peptide toxin, ω-conotoxin GVIA, and P-type channels are blocked by the peptide ω-agatoxin IVA from the venom of the funnel web spider, *Agelenopsis aperta*. A fourth type of high voltage-activated calcium channel (Q-type) has been described, although whether the Q- and P-type channels are distinct molecular entities is controversial (Sather, W. A. et al. *Neuron* (1995) 11:291–303; Stea, A. et al. *Proc Natl Acad Sci USA* (1994) 91:10576–10580). Several types of calcium conductances do not fall neatly into any of the above categories and there is variability of properties even within a category suggesting that additional calcium channels subtypes remain to be classified.

Biochemical analyses show that neuronal high-threshold calcium channels are heterooligomeric complexes consisting of three distinct subunits ($\alpha_1$, $\alpha_2\delta$ and $\beta$) (reviewed by De Waard, M. et al. *Ion Channels* (1997) vol. 4, Narahashi, T. ed. Plenum Press, New York). The $\alpha_1$ subunit is the major pore-forming subunit and contains the voltage sensor and binding sites for calcium channel antagonists. The mainly extracellular $\alpha_2$ is disulfide-linked to the transmembrane $\delta$ subunit and both are derived from the same gene and are proteolytically cleaved in vivo. The $\beta$ subunit is a nonglycosylated, hydrophilic protein with a high affinity of binding to a cytoplasmic region of the $\alpha_1$ subunit. A fourth subunit, $\gamma$, is unique to L-type calcium channels expressed in skeletal muscle T-tubules. The isolation and characterization of γ-subunit-encoding cDNAs is described in U.S. Pat. No. 5,386,025 which is incorporated herein by reference.

Recently, each of these $\alpha_1$ subtypes has been cloned and expressed, thus permitting more extensive pharmacological studies. These channels have been designated $\alpha_{1A}$–$\alpha_{1H}$ and $\alpha_{1S}$ and correlated with the subtypes set forth above. $\alpha_{1A}$ channels are of the P/Q type; $\alpha_{1B}$ represents N; $\alpha_{1C}$, $\alpha_{1D}$ and $\alpha_{1S}$ represent L; $\alpha_{1E}$ represents a novel type of calcium conductance, and $\alpha_{1G}$ and $\alpha_{1H}$ represent two members of the T-type family, reviewed in Stea, A. et al. in Handbook of Receptors and Channels (1994), North, R. A. ed. CRC Press; Perez-Reyes, et al. *Nature* (1998) 391:896–900. Bech-Hansen et al., *Nature Neurosci* (1998) 1:264–267.

U.S. Ser. No. 09/107,037 filed Jun. 30, 1998 describes compounds containing benzhydril and 6-membered heterocyclic moieties that show calcium-channel blocking activity, wherein certain members of the disclosed genus are specific to N-type channels. The present invention is directed to compounds structurally related to farnesol whose activity is also N-type specific at low concentrations. Farnesol has previously been shown to be a calcium-channel blocker when used in the micromolar range and to show a preference for inhibition of L-type receptors (Roullet, J.-B., et al., *J Biol Chem* (1997) 272:32240–32246. This demonstrated activity is exhibited as "open channel" blockage; that is, channels that have been activated by depolarization show inhibited calcium ion flow. This is in contrast to the inactivated channel block which is exhibited, but at nanomolar concentrations, by farnesol and its related compounds and is specific to the N-type channel. Accordingly, these compounds which, like farnesol, promote the inactivation of the N-type channels, preferably at physiological background potential conditions, are useful in treating conditions associated with N-type channel activity, such as stroke and pain.

DISCLOSURE OF THE INVENTION

The invention relates to compounds useful in treating conditions such as stroke, chronic and acute pain, epilepsy, hypertension, cardiac arrhythmias, and other indications associated with calcium physiology. The compounds of the invention are related structurally to farnesol and can contain substituents that enhance the specificity of the inactivation inhibition of N-type channels. Thus, in one aspect, the invention is directed to therapeutic methods that employ compounds containing a straight backbone carbon chain of 8–16C optionally substituted with 1–5 alkyl groups (1–6C). The compounds may optionally be functionalized at one terminus with halo, —OR, —SR, —NR$_2$, —OOCR, —NROCR, where R is H or alkyl (1–6C) or phosphate or pyrophosphate, or a terminal carbon is optionally in the form of —COOR, —CONR$_2$ or —COR, where R is H or alkyl (1–6C). The backbone chain may optionally contain 1–4 π-bonds or the epoxides thereof.

The invention is directed to methods to antagonize calcium channel activity using these compounds and thus to treat associated conditions. It will be noted that the conditions may be associated with abnormal calcium channel activity, or the subject may have normal calcium channel function which nevertheless results in an undesirable physical or metabolic state. In another aspect, the invention is directed to pharmaceutical compositions containing these compounds.

The invention is also directed to combinatorial libraries containing the compounds of the invention and to methods to screen these libraries for members containing particularly potent calcium channel inactivating activity or for members that antagonize other channels.

MODES OF CARRYING OUT THE INVENTION

Figure 1A:
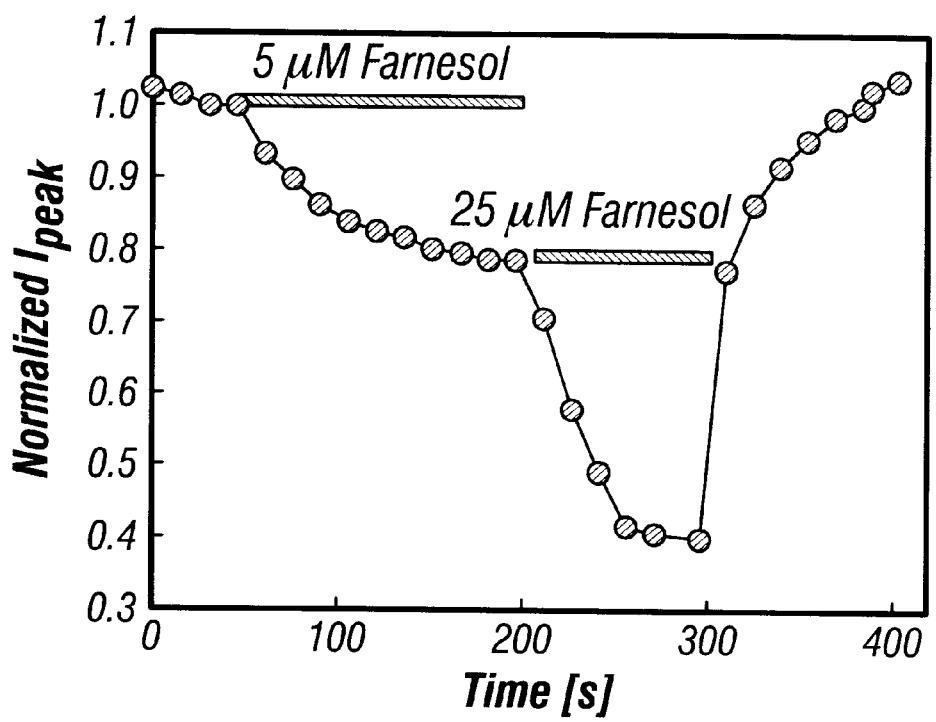
FIG. 1, panels A–E, shows the effect of farnesol in micromolar concentrations on open-channel blocking in various types of calcium-channels.
Figure 1B:
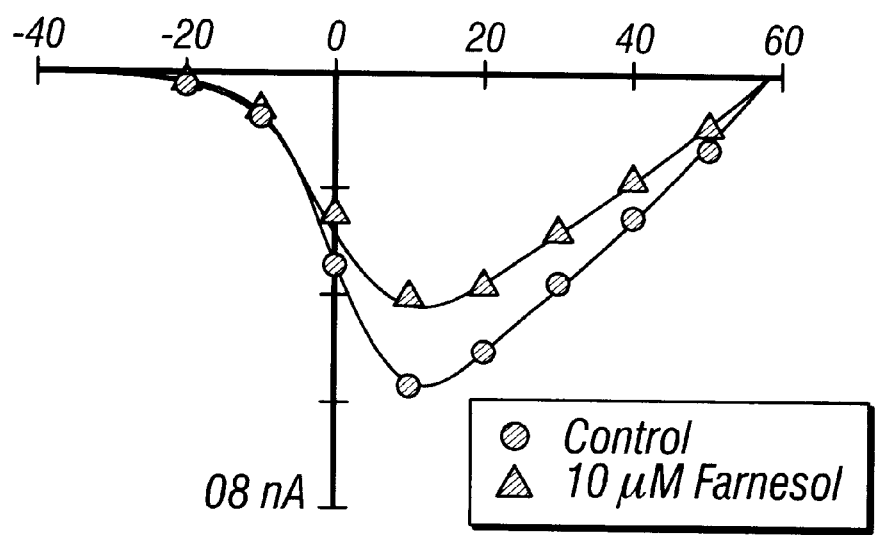
Figure 1C:
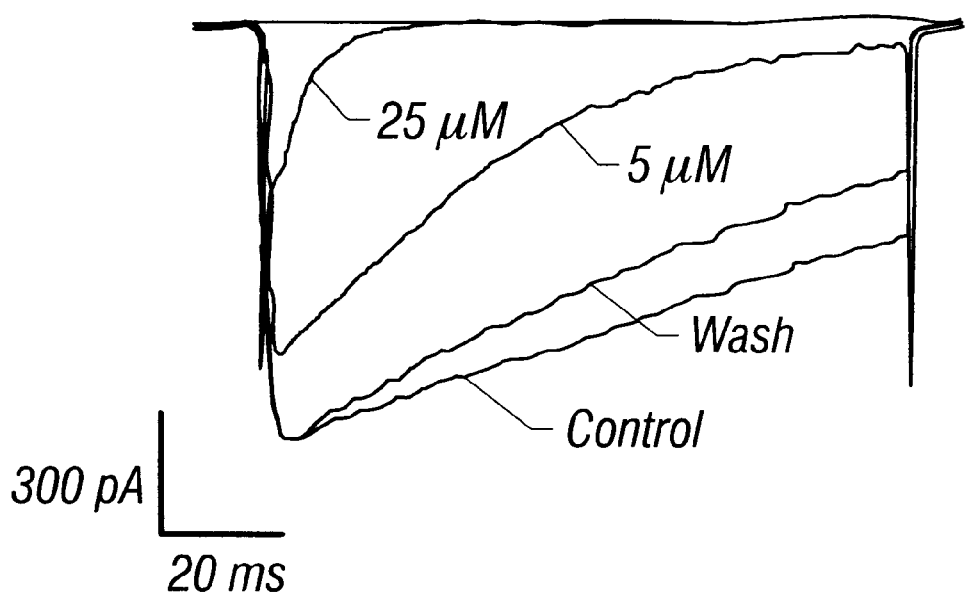
Figure 1D:
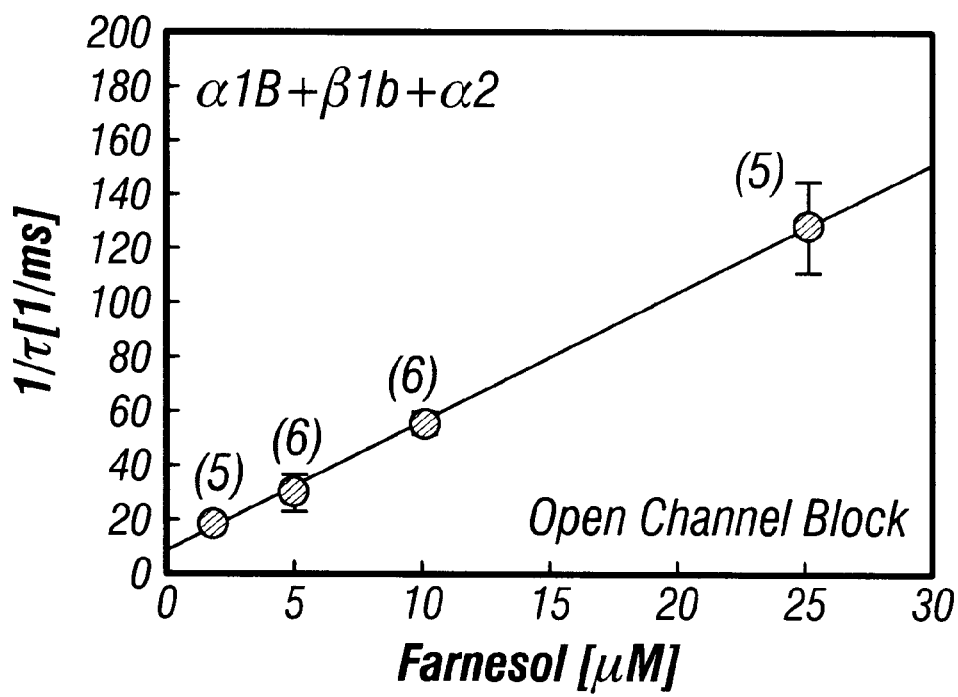
Figure 1E:
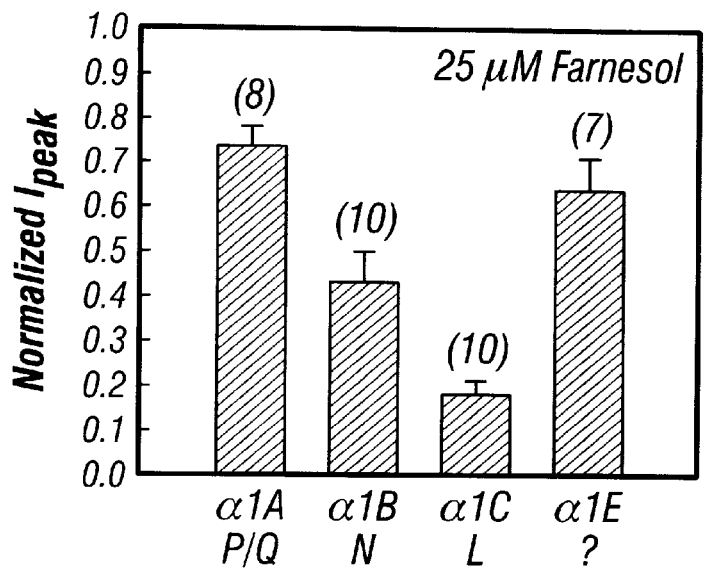

The compounds useful in the methods of the invention exert their desirable effects through their ability to specifically promote inactivation of N-type calcium channels.

There are two distinguishable types of calcium channel inhibition. The first, designated "open channel blockage," is demonstrated when displayed calcium channels are maintained at an artificially negative resting potential of about −100 mV (as distinguished from the typical endogenous resting maintained potential of about −70 mV). When the displayed channels are abruptly depolarized under these conditions, calcium ions are caused to flow through the channel and exhibit a peak current flow which then decays. Open channel blocking inhibitors diminish the current exhibited at the peak flow as well as accelerate the rate of decay. A second type of block is referred to herein as "inactivation inhibition." When maintained at less negative resting potentials, such as the physiologically important potential of −70 mV, a certain percentage of the receptor channels may undergo conformational change, rendering them incapable of being activated—i.e., opened—by the abrupt depolarization. Thus, the peak current due to calcium ion flow will be diminished not because the open channel is blocked, but because some of the channels are unavailable for opening (inactivated). "Inactivation" type inhibitors increase the percentage of receptors that are inactivated. With regard to the compounds of the present invention, this type of inhibition is typically exhibited at lower concentrations than those required for open channel blockage and is highly specific for N-type channel. The level of specificity exhibited by various compounds of the invention is determined by the nature of the substituents on the straight-chain backbone.

While the compounds of the invention generally show channel inhibitions, the availability of a multiplicity of calcium channel inhibitors permits a nuanced selection of compounds for particular disorders. Thus, the availability of this class of compounds provides not only a genus of general utility in indications that are affected by excessive calcium channel activity, but also provides a large number of compounds which can be mined and manipulated for specific interaction with particular forms of calcium channels. The availability of recombinantly produced calcium channels of the $\alpha_{1A}$–$\alpha_{1H}$ and $\alpha_{1S}$ types set forth above, facilitates this selection process. Dubel, S. J. et al. *Proc Natl Acad Sci USA* (1992) 89:5058–5062; Fujita, Y. et al. *Neuron* (1993) 10:585–598; Mikami, A. et al. *Nature* (1989) 340:230–233; Mori, Y. et al. *Nature* (1991) 350:398–402; Snutch, T. P. et al. *Neuron* (1991) 7:45–57; Soong, T. W. et al. *Science* (1993) 260:1133–1136; Tomlinson, W. J. et al. *Neuropharmacology* (1993) 32:1117–1126; Williams, M. E. et al. *Neuron* (1992) 8:71–84; Williams, M. E. et al. *Science* (1992) 257:389–395; Perez-Reyes, et al. *Nature* (1998) 391:896–900. Bech-Hansen et al., *Nature Neurosci* (1998) 1:264–267.

Thus, while it is known that calcium channel activity is involved in a multiplicity of disorders, the types of channels associated with particular conditions is the subject of ongoing data collection. The association of, for example, N-type channels, as opposed to other types, in a specific condition would indicate that compounds of the invention which specifically target N-type receptors are most useful in this condition. Many of the members of the genus of compounds of included in the invention target N-type channels specifically. Other members of the genus are less specific.

Among the conditions associated in which blocking excessive calcium would be of therapeutic value are stroke, epilepsy, and chronic and acute pain. Other cardiovascular conditions include hypertension and cardiac arrhythmias. Calcium is also implicated in other neurological disorders such as migraine, epilepsy and certain degenerative disorders.

The availability of the libraries containing the compounds of the invention also provides a source of compounds which may be screened for inactivation inhibition with regard to additional ion channels and receptors. These channels and receptors are also associated with conditions that are susceptible to treatment. Blockers of sodium channels, for example, are useful as local anesthetics, and in treating cardiac arrhythmias, as anticonvulsants, and in treating hyperkalemic periodic paralysis. Potassium channel blockers are useful in treating hypertension and cardiac arrhythmias; various other receptors are associated with psychoses, schizophrenia, depression, and apnea. Thus, the library of compounds of the invention is useful in standard screening techniques as a source of effective pharmaceutical compounds.

The compounds of the invention are defined in terms of the embodiments of permitted substituents, as well as by chain length and degree of unsaturation:

The preferred length of the backbone chain is 10–18C, preferably 12–15C. It is preferred that the compounds contain 1–5 alkyl substituents, preferably ethyl or methyl, most preferably methyl, wherein the positions of the substitutions are separated by 2–3C, preferably 3C. The compounds of the invention preferably contain 0, 1, 2 or 3 π-bonds which are not conjugated to each other. Preferred termini of the chain include halo, —OR, —OOCR, and —NR$_2$ wherein R is H or 1–6C, preferably halo, or embodiments wherein the termini are unsubstituted. Also preferred are compounds containing 0, 1, 2 or 3 π-bonds which are not conjugated to each other. Particularly preferred spacing of the π-bonds is 2–3 intervening carbons, preferably 2.

The invention compounds may also be supplied, where appropriate, as pharmaceutically acceptable salts. Pharmaceutically acceptable salts, where the compounds contain amino groups, include the acid addition salts which can be formed from inorganic acids such as hydrochloric, sulfuric, and phosphoric acid or from organic acids such as acetic, propionic, glutamic, glutaric, as well as acid ion-exchange resins. When the compounds contain acidic groups, salts may be formed from inorganic bases such as potassium or sodium hydroxide, calcium hydroxide, or magnesium hydroxide and from organic bases such as caffeine.

UTILITY AND ADMINISTRATION

For use as treatment of animal subjects, the compounds of the invention can be formulated as pharmaceutical or veterinary compositions. Depending on the subject to be treated, the mode of administration, and the type of treatment desired—e.g., prevention, prophylaxis, therapy; the compounds are formulated in ways consonant with these parameters. A summary of such techniques is found in Remington's *Pharmaceutical Sciences,* latest edition, Mack Publishing Co., Easton, Pa.

In general, for use in treatment, the compounds of the invention may be used alone, as mixtures of two or more compounds of the invention or in combination with other pharmaceuticals. Depending on the mode of administration, the compounds will be formulated into suitable compositions to permit facile delivery.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677.

Systemic administration may also include relatively noninvasive methods such as the use of suppositories, transdermal patches, transmucosal delivery and intranasal administration. Oral administration is also suitable for compounds of the invention. Suitable forms include syrups, capsules, tablets, as in understood in the art.

For administration to animal or human subjects, the dosage of the compounds of the invention is typically 0.1–100 μg/kg. However, dosage levels are highly dependent on the nature of the condition, the condition of the patient, the judgment of the practitioner, and the frequency and mode of administration.

Screening Methods

The compounds of the invention can be synthesized individually using methods known in the art per se, or as members of a combinatorial library.

Synthesis of combinatorial libraries is now commonplace in the art. Suitable descriptions of such syntheses are found, for example, in Wentworth, Jr., P. et al. *Current Opinion in Biol* (1993) 9:109–115; Salemme, F. R. et al. *Structure* (1997) 5:319–324. The libraries contain compounds with various substituents and various degrees of unsaturation, as well as different chain lengths. The libraries, which contain, as few as 10, but typically several hundred members to several thousand members, may then be screened for compounds which are particularly effective against a specific subtype of calcium channel. In addition, using standard screening protocols, the libraries may be screened for compounds which block additional channels or receptors such as sodium channels, potassium channels and the like.

Methods of performing these screening functions are well known in the art. Typically, the receptor to be targeted is expressed at the surface of a recombinant host cell such as human embryonic kidney cells. The ability of the members of the library to bind the receptor or channel is measured, for example, by the ability of the compound in the library to displace a labeled binding ligand such as the ligand normally associated with the receptor or an antibody to the receptor. More typically, ability to antagonize the receptor is measured in the presence of calcium ion and the ability of the compound to interfere with the signal generated is measured using standard techniques.

In more detail, one method involves the binding of radiolabeled agents that interact with the calcium channel and subsequent analysis of equilibrium binding measurements including, but not limited to, on rates, off rates, $K_d$ values and competitive binding by other molecules. Another method involves the screening for the effects of compounds by electrophysiological assay whereby individual cells are impaled with a microelectrode and currents through the calcium channel are recorded before and after application of the compound of interest. Another method, high-throughput spectrophotometric assay, utilizes loading of the cell lines with a fluorescent dye sensitive to intracellular calcium concentration and subsequent examination of the effects of compounds on the ability of depolarization by potassium chloride or other means to alter intracellular calcium levels.

As described above, a more definitive assay can be used to distinguish inhibitors of calcium flow which operate as open channel blockers, as opposed to those that operate by promoting inactivation of the channel. The methods to distinguish these types of inhibition are more particularly described in the examples below. In general, open-channel blockers are assessed by measuring the level of peak current when depolarization is imposed on a background resting potential of about −100 mV in the presence and absence of the candidate compound. Successful open-channel blockers will reduce the peak current observed and accelerate the decay of this current. Compounds that are inactivated channel blockers are determined by their ability to shift the voltage dependence of inactivation towards more negative potentials. This is also reflected in their ability to reduce peak currents at more depolarized holding potentials(e.g., −70 mV).

The following examples are intended to illustrate but not to limit the invention.

EXAMPLE 1

Transfection of HEK Cells

Human embryonic kidney TSA 201 cells were grown in standard DMEM medium, supplemented with 10% fetal bovine serum and 0.4 mg/ml neomycin. The cells were grown to 80% confluency, split with trypsin EDTA and plated on glass coverslips at 10% confluency 12 hours prior to transfection. Immediately prior to transfection, the medium was replaced and the cells were transiently transfected with cDNAs encoding calcium channel $\alpha_{1B}$, $\beta_{1b}$ and $\alpha_2$ subunits (at a 1:1:1 molar ratio) using a standard calcium phosphate protocol. After 12 hours, the medium was replaced with fresh DMEM and the cells were allowed to recover for 12 hours. Subsequently the cells were incubated at 28° C. in 5% $CO_2$ for 1–2 days prior to recording. Human embryonic kidney cells stably expressing N-type $\alpha_{1B}$+$\alpha_2$+$\beta_{1b}$ were maintained and plated for electrophysiological recordings as described by Zamponi, G. W. et al., *Nature* (1997) 385:442–446.

For some experiments, cells were prepared wherein the $\alpha_{1B}$ unit was replaced by $\alpha_{1A}$ (P/Q type) $\alpha_{1C}$ (type L) or $\alpha_{1E}$ (undefined). $\alpha_{1B}$ represents N-type.

EXAMPLE 2

Methods of Analysis

Immediately prior to recording, individual cover slips were transferred to a 3 cm culture dish containing an external recording solution. The external recording solution was 20 mM $BaCl_2$, 1 mM $MgCl_2$, 10 mM HEPES, 40 mM TEACl, 10 mM glucose, 65 mM CsCl (pH 7.2) or 5 mM $BaCl_2$, 1 mM $MgCl_2$, 10 mM HEPES, 40 mM TEACl, 10 mM glucose, 87.5 mM CsCl (pH 7.2). Patch pipettes (Sutter borosilicate glass, BF150-86-15) were pulled using a Sutter P-87 microelectrode puller, fire-polished using a Narashige microforge, and showed typical resistances of 2–4 MΩ. The internal pipette solution is 105 mM CsCl, 25 mM TEACl, 1 mM $CaCl_2$, 11 mM EGTA, 10 mM HEPES (pH 7.2). Whole cell patch clamp experiments were performed using an Axopatch 200B amplifier (Axon Instruments, Burlingame, Calif.) linked to an IBM compatible personal computer equipped with pCLAMP 6.0 software. Currents were typically elicited from a holding potential of −100 mV to various test potentials. The compounds to be tested were prepared as stock solutions in ethanol and diluted into the recording solution at the appropriate final concentrations, and perfused directly onto the cells using a gravity driven microperfusion system. At the applicable concentrations, ethanol by itself had no effect on calcium channel activity. Data were filtered at 1 kHz and recorded directly on the hard drive of a personal computer. The data were analyzed using ClampFit (Axon Instruments). Curve fitting was carried out in Sigmaplot 4.0 (Jandel Scientific). Steady state inactivation curves were fitted with a Boltzman equation, $$I_{peak(normalized)}=1/(1+\exp((V-V_h)Z/25.6))$$

where V and $V_h$ are respectively the conditioning and the half activation potential, and Z is a slope factor.

EXAMPLE 3
Open-Channel Blocking by Farnesol

The stably expressed N-type receptors in HEK293 cells, prepared as in Example 1, were tested at various concentrations of farnesol by step depolarizations from the holding potential of −100 mV to the test potential of +20 mV. Panel C of FIG. 1 shows a typical response elicited by a single depolarization wherein the current is increased to peak value within 2.5 msec and then decays to its resting level at various rates depending on conditions. As shown, the presence of 5 μM or 25 μM farnesol both diminished the current at peak value and accelerated time to decay to the resting level. In a series of such depolarizations at farnesol concentrations of 5 μM and 25 μM shown in panel A, it is apparent that the normalized peak height is diminished in the presence of 5 μM farnesol and further dramatically diminished in the presence of 25 μM farnesol. Upon removal of the farnesol, the ability to obtain peak currents is regenerated.

Panel B shows the relationship of the depolarization voltage to the current generated before and after addition of 10 μM farnesol. The current/voltage relationship was fitted with the Boltzman relation (solid lines). There appears to be no dependence of the position of peak amplitude with respect to depolarization voltage on the presence of farnesol.

Panel D represents a kinetic analysis of the current wave form shown in Panel C. the Y-axis shows the inverse of the time constant for current decay corrected for the control inactivation rate of the channel plotted as a function of farnesol concentration. A linear relationship showing an intercept of 7.6 and a slope of 4.8, r=1 is obtained consistent with speeding of the time course of inactivation due to a rapid 1:1 open channel block developing during the test pulse.

Panel E shows these open channel blocking effects of 25 μM farnesol for various receptors using a resting potential of −100 mV on current amplitudes. The numbers in parentheses reflect the number of experiments; the error bars are standard errors. All types of channels show diminished peak heights at this concentration. It appears that L-type channels are preferentially inhibited by open channel block.

EXAMPLE 4
The Effect of Farnesol on Inactivation

Figure 2:
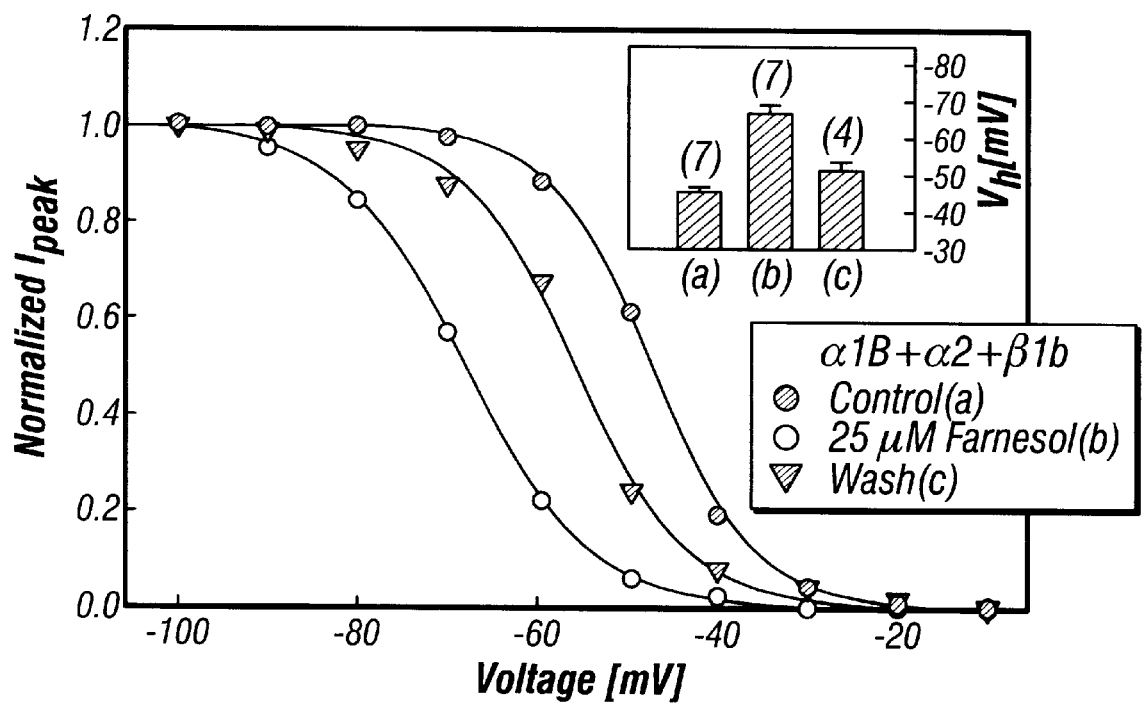
FIG. 2 shows the selective inactivation of N-type receptors at 25 μM farnesol.
Figure 3A:
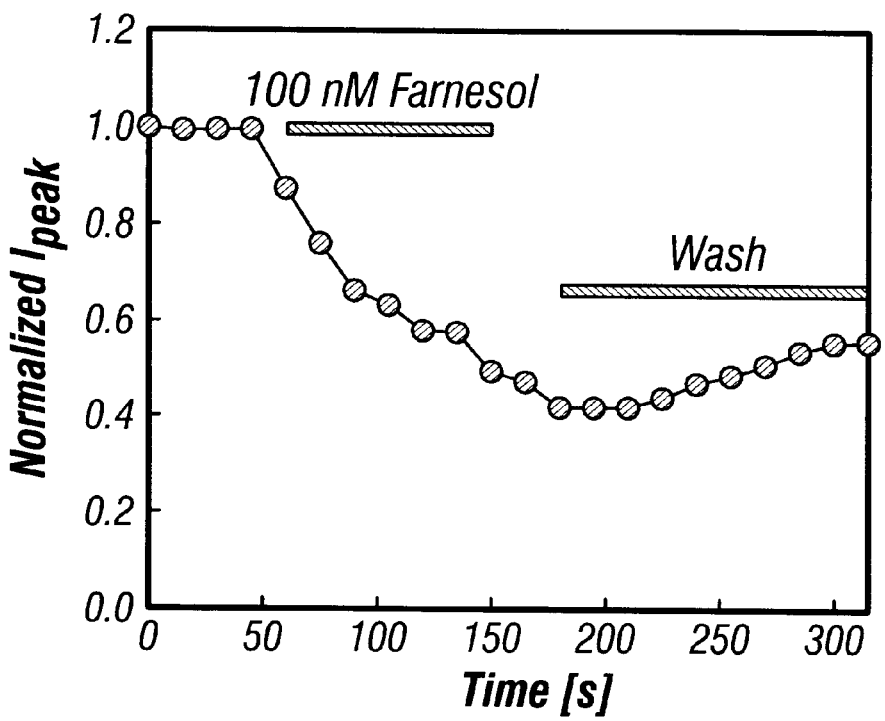
FIG. 3, panels A–D, shows the effect of nanomolar concentrations of farnesol on inactivation of various calcium channel types.
Figure 3B:
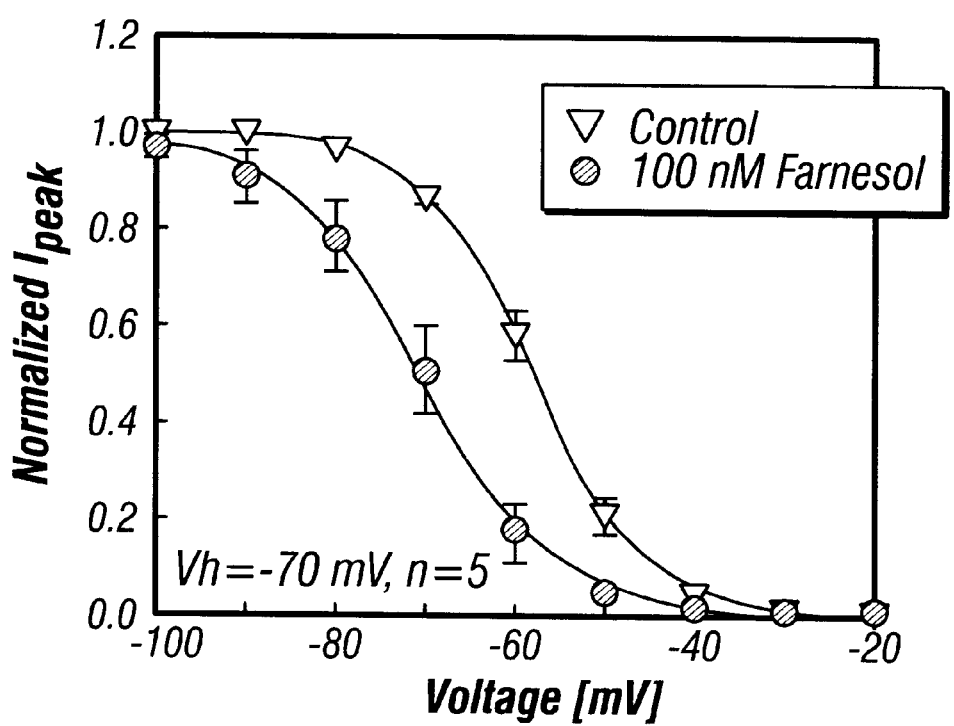
Figure 3C:
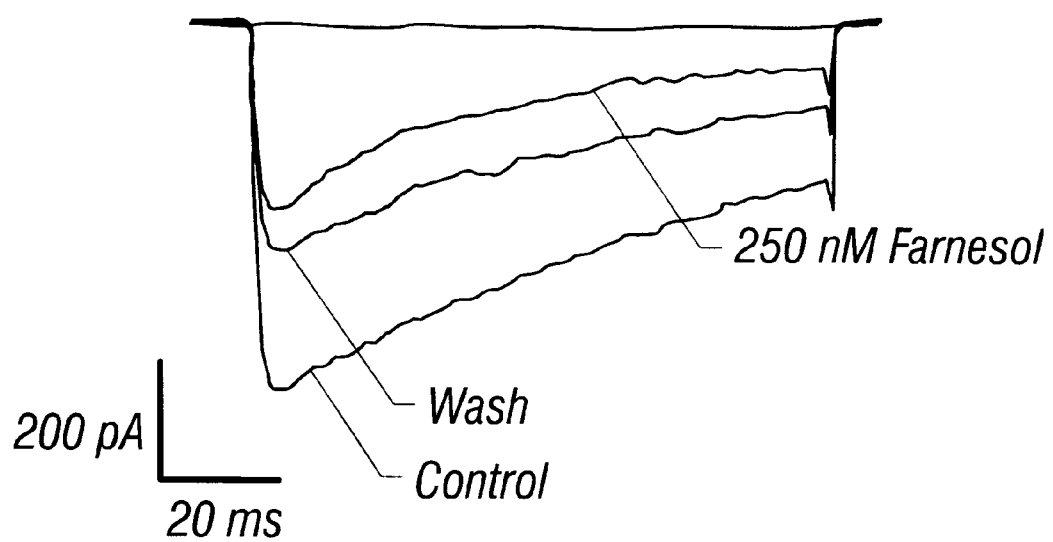
Figure 3D:
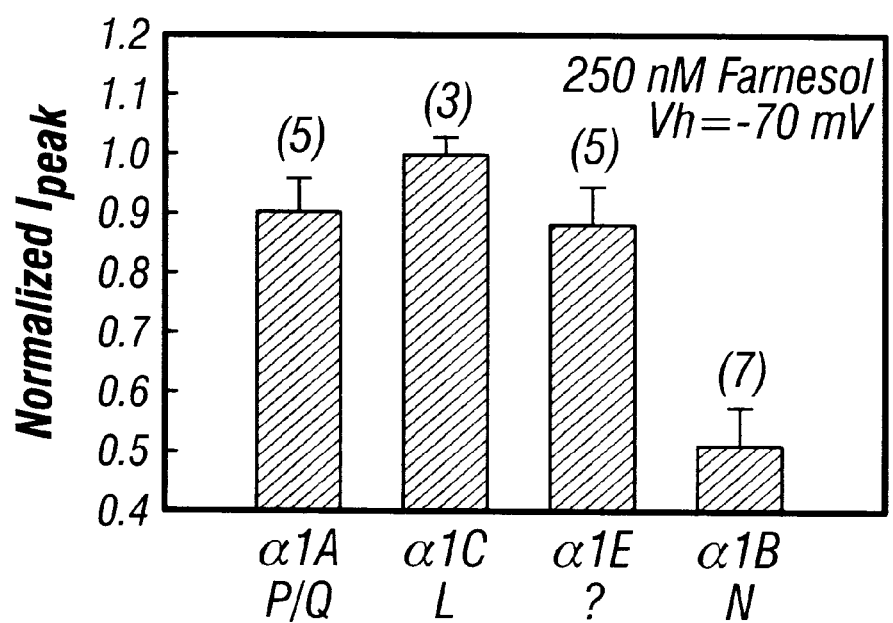

The effect of farnesol on inactivation of the N-type channel at various resting potentials was determined. Currents were elicited by stepping from various holding potentials of 5-second duration to a test potential of +20 mV. The data were obtained from the same cell and fitted according to the Boltzman relation (control: $V_h$=−47.9 mV, Z=4.4; 25 μM farnesol: $V_h$=−68.7 mV, Z=3.8; Wash: $V_h$=−56.5 mV, Z=4.0). As shown in FIG. 2, at a starting potential of −80 mV, neither the control nor the washed cells showed diminished potential (all peak potentials were normalized to their value at −100 mV resting potential). However, in the presence of 25 μM farnesol, the peak value was diminished to 80% of the base value. At a resting potential of −70 mV, the peak current value in the presence of 25 μM farnesol was reduced to 50%. The control and wash showed little diminution. The inset shows the mean values of the resting potential that diminishes peak currents to ½ their value when −100 mV is used ($V_{0.5}$) before farnesol was added, while farnesol was present, and after farnesol was washed out of the system. This occurs at −70 mV for the sample where farnesol is present and at much lower resting potentials prior to addition or after wash. Thus, farnesol at this concentration shows a shift in $V_{0.5}$ of about 20 mV.

Further experiments verifying the ability of farnesol to exert an inactivation-based inhibition were conducted. FIG. 3, panel A shows the time course of the peak current block by 100 nM farnesol at a resting potential of −70 mV, which closely reflects a nerve cell resting potential. The time course of the development of the current amplitude diminution is slower than that obtained at a resting potential of −100 mV and the recovery is much slower from the effect exhibited by open-chain blockage. Compare FIG. 1, panel A at 25 μM farnesol (an open-channel blocking effect) with panel A of FIG. 3. This is also shown in a typical inactivation curve as set forth in panel C of FIG. 3 determined in the presence of 250 nM farnesol. The kinetics of the recovery times of the current flow to resting appear similar in all cases. This curve was determined from a holding potential of −70 mV to a test potential of +10 mV in the presence and absence of 250 nM farnesol. At this concentration the effect of farnesol does not appear to be completely reversible.

Panel B shows the inactivation effect of 100 nM farnesol on the N-type channel under conditions similar to those of FIG. 2. Again, the $V_{0.5}$ is −70 mV.

Finally, panel D shows the specificity of this inactivation effect. The values plotted are the peak current values normalized to a resting potential of −100 mV when the resting potential is −70 mV in the presence of 250 nM farnesol. Only the N-type channels show substantially diminished values.

EXAMPLE 4
Additional Inactivation Inhibitors

Various farnesol-related compounds were tested for their ability to exhibit open-channel blockage and to promote inactivation specific to the N-type channel. The results are shown in Table 1.

TABLE 1

| Compound | Open/Resting Block (determined at 10 μM) | Inactivated Block (shift in $V_{0.5}$) |
|---|---|---|
| farnesol | 60% block | 10–25 mV |
| farnesyl acetate | 90–100% block | ~20 mV |
| farnesyl bromide | 20–30% block | ~20 mV |
| farnesyl pyrophosphate | Not active | n.d. |
| juvenile hormone III | Not active | ~10 mV |
| tetramethylpentadecane | <10% block | ~10 mV |
| dodecylamine | 90–100% block | ~10 mV |
| dodecane | 10–20% block | ~10 mV |
| decylamine | >80% block | ~10 mV |

As seen, farnesyl bromide, juvenile hormone III, tetramethylpentadecane, and dodecane are able to promote substantial inactivation-type inhibition, specific to the N-type receptor, but are relatively lacking in the nonspecific open-channel blocking activity. Thus, the compounds of the invention offer the opportunity of enhanced specificity without undesired nonspecific open channel block.

What is claimed is:

1. A method of treating conditions associated with N-type calcium channel activity in a subject which method comprises adminstering to a subject in need of such treatment a compound comprising in an amount sufficient to effect inactiviation inhibition of said N-type channel, said compound comprising a straight backbone carbon chain of 8–16C, optionally substituted with 1–15 alkyl groups (1–6C);

said chain optionally functionalized at one terminus with halo, —OR, SR, $NR_2$, —OOCR, —NROCR wherein R is alkyl (1–6C), or phosphate or pyrophosphate, or functionalized wherein a terminal carbon is optionally in the form or —COOR, —$CONR_2$ or —COR wherein R is alkyl (1–16C); and wherein said chain may optionally contain 1–4 π-bonds or the epoxides thereof;

with the proviso that said compound is other than farnesol or geraniol.

2. The method of claim 1 wherein said compound has a backbone chain of 12–15C.

3. The method of claim 1 wherein said backbone chain is substituted with 1–5 alkyl groups and wherein said alkyl groups are methyl or ethyl.

4. The method of claim 1 wherein said chain is unfunctionalized or wherein said chain is functionalized at one terminus with halo.

5. The method of claim 1 wherein said chain contains an epoxide.

6. The method of claim 1 wherein said compound is farnesyl bromide, tetramethylpentadecane, or dodecane.

7. A pharmaceutical composition for use in treating conditions characterized by N-type calcium channel activity which composition comprises, in admixture with a pharmaceutically acceptable excipient, a dosage amount of a compound effective to result in inactivation inhibition of said N-type calcium channel, said compound comprising a straight backbone carbon chain of 8–16C, optionally substituted with 1–5 alkyl groups (1–6C);

said chain optionally functionalized at one terminus with halo, —OR, SR, $NR_2$, —OOCR, —NROCR wherein R is alkyl (1–6C), or phosphate or pyrophosphate, or functionalized wherein a terminal carbon is optionally in the form or —COOR, —$CONR_2$ or —COR wherein R is (1–6C); and wherein said chain may optionally contain 1–4 π-bonds or the epoxides thereof;

with the proviso that said compound is other than farnesol or geraniol.

8. The composition of claim 7 wherein said compound has a backbone chain of 12–15C.

9. The composition of claim 7 wherein said backbone chain is substituted with 1–5 alkyl groups and wherein said alkyl groups are methyl or ethyl.

10. The composition of claim 7 wherein said chain is unfunctionalized or wherein said chain is functionalized at one terminus with halo.

11. The composition of claim 7 wherein said chain contains an epoxide.

12. The composition of claim 7 wherein said compound is farnesyl bromide, tetramethylpentadecane, or dodecane.

13. A method to identify a compound which antagonizes an N-type calcium ion channel which method comprises contacting host cells displaying said N-type calcium ion channel in the presence of an agonist for said channel and with the members of a compound library;

assessing the ability of the members of the library to affect the response of the channel to its agonist; and identifying as an antagonist any member of the library which diminishes the response of the channel to its agonist;

wherein said compound library comprises at least ten different compounds each of said compounds comprising a straight backbone carbon chain of 8–16C, optionally substituted with 1–5 alkyl groups (1–6C);

said chain optionally functionalized at one terminus with halo, —OR, —SR, —$NR_2$, —OOCR, —NROCR wherein R is alkyl (1–6C), or phosphate or pyrophosphate, or functionalized wherein a terminal carbon is optionally in the form of —COOR, —$CONR_2$ or —COR where R is alkyl (1–6C); and wherein said chain may optionally contain 1–4 π-bonds or the epoxides thereof.

14. The method of claim 1 wherein said conditions comprise neurological disorders.

15. The method of claim 14 wherein said neurological disorder is acute pain, chronic pain or the resultant of stroke.

16. The composition of claim 7 wherein said conditions comprise neurological disorders.

17. The composition of claim 16 wherein said neurological disorder is acute pain, chronic pain or the resultant of stroke.

* * * * *